United States Patent
Sheil et al.

(10) Patent No.: US 8,960,128 B2
(45) Date of Patent: Feb. 24, 2015

(54) TOPICAL ANESTHETIC COMPOSITION

(75) Inventors: Meredith Sheil, Hunters Hill (AU); Allan Giffard, Yarra Glen (AU); Charles Robert Olsson, Gordon (AU)

(73) Assignee: Animal Ethics Pty Ltd, Crestmead (AU)

( * ) Notice: Subject to any disclaimer, the term of this patent is extended or adjusted under 35 U.S.C. 154(b) by 1675 days.

(21) Appl. No.: 11/856,171

(22) Filed: Sep. 17, 2007

(65) Prior Publication Data

US 2008/0085245 A1   Apr. 10, 2008

Related U.S. Application Data

(63) Continuation-in-part of application No. PCT/AU2006/000336, filed on Mar. 15, 2006.

(30) Foreign Application Priority Data

| Mar. 15, 2005 | (AU) | ................................. | 2005901250 |
| May 6, 2005 | (AU) | ................................. | 2005902296 |
| Sep. 14, 2005 | (AU) | ................................. | 2005905062 |
| Dec. 12, 2005 | (AU) | ................................. | 2005906965 |

(51) Int. Cl.

| *A61K 38/00* | (2006.01) |
| *A61L 26/00* | (2006.01) |
| *A61K 9/00* | (2006.01) |
| *A61K 9/06* | (2006.01) |
| *A61K 31/167* | (2006.01) |
| *A61K 31/445* | (2006.01) |
| *A61K 31/137* | (2006.01) |
| *A61K 31/14* | (2006.01) |
| *A61K 31/245* | (2006.01) |
| *A61K 33/04* | (2006.01) |
| *A61K 47/26* | (2006.01) |
| *A61K 47/38* | (2006.01) |

(52) U.S. Cl.

CPC ........... *A61L 26/0066* (2013.01); *A61K 9/0017* (2013.01); *A61K 9/06* (2013.01); *A61K 31/167* (2013.01); *A61K 31/445* (2013.01); *A61L 26/008* (2013.01); *A61K 9/0014* (2013.01); *A61K 31/137* (2013.01); *A61K 31/14* (2013.01); *A61K 31/245* (2013.01); *A61K 33/04* (2013.01); *A61K 47/26* (2013.01); *A61K 47/38* (2013.01); *A61L 26/0076* (2013.01); *A61L 2300/402* (2013.01); *A61L 2300/404* (2013.01); *A61L 2300/418* (2013.01); *A61L 2300/442* (2013.01); *A61L 2300/45* (2013.01); *A61L 2300/41* (2013.01)

USPC .......... 119/416; 119/174; 119/712; 424/10.3; 424/10.31

(58) Field of Classification Search

CPC .............. A61K 9/0017; A61K 31/167; A61K 31/1445; A61K 9/06; A61L 26/0066; A61L 26/008; A61L 2300/402; A61L 2300/404; A61L 2300/442; A61L 2300/45

See application file for complete search history.

(56) References Cited

U.S. PATENT DOCUMENTS

| 3,832,460 | A | 8/1974 | Kosti |
| 4,248,855 | A | 2/1981 | Blank et al. |
| 5,098,417 | A | 3/1992 | Yamakazi et al. |
| 5,563,153 | A | 10/1996 | Mueller et al. |
| 5,585,398 | A | 12/1996 | Ernst |
| 5,804,213 | A | 9/1998 | Rolf et al. |
| 5,827,529 | A | 10/1998 | Ono et al. |
| 5,942,543 | A | 8/1999 | Ernst |
| 6,075,059 | A | 6/2000 | Reader |
| 6,146,654 | A | 11/2000 | Kubo |
| 6,159,498 | A | 12/2000 | Tapolsky et al. |
| 6,295,469 | B1 * | 9/2001 | Linkwitz et al. ................ 604/20 |
| 6,375,963 | B1 | 4/2002 | Repka et al. |
| 6,562,363 | B1 * | 5/2003 | Mantelle et al. .............. 424/434 |
| 6,620,852 | B2 | 9/2003 | Brogan et al. |
| 2002/0006435 | A1 * | 1/2002 | Samuels et al. ............... 424/449 |
| 2003/0059379 | A1 | 3/2003 | Andersen et al. |
| 2003/0185873 | A1 | 10/2003 | Chasin et al. |
| 2003/0232091 | A1 | 12/2003 | Shefer et al. |

(Continued)

FOREIGN PATENT DOCUMENTS

| AU | 524658 | 11/1978 |
| AU | 647784 | 3/1991 |

(Continued)

OTHER PUBLICATIONS

Sutherland et al., Effect of local anaesthetic combined with wound cauterisation on the cortisol response to dehorning calves, Aus Vet. J. Mar. 2002;80(3); 165-167.

(Continued)

*Primary Examiner* — Frederick Krass
*Assistant Examiner* — Nannette Holloman
(74) *Attorney, Agent, or Firm* — Venable LLP; Stefan J. Kirchanski

(57) ABSTRACT

A method for providing anesthesia to a subject having a wound, such as a laceration, a surgical incision, an ulcer, an abrasion or a burn, said method comprising the step of applying topically to the wound a composition comprising: at least one local anesthetic agent; a hydrophilic or hydroalcoholic gelling agent; an antiseptic agent; a vasoconstrictor; and a detectable marker such as a food dye, wherein when the composition is topically applied to the wound of the subject the presence of the anesthetic agent on the subject is indicated by the detectable marker. The method has been developed primarily for anaesthetizing open wounds of animals, particularly those caused by husbandry procedures.

16 Claims, No Drawings

(56) References Cited

U.S. PATENT DOCUMENTS

| | | | |
|---|---|---|---|
| 2004/0086575 A1* | 5/2004 | Smith | 424/643 |
| 2004/0101582 A1* | 5/2004 | Wolicki | 424/760 |
| 2005/0256187 A1 | 11/2005 | Liedtke | |

FOREIGN PATENT DOCUMENTS

| | | | |
|---|---|---|---|
| EP | 0040862 | 2/1981 | |
| EP | 1550441 | 6/2005 | |
| GB | 2198642 | 6/1988 | |
| GB | 2288734 | 1/1995 | |
| GB | 2414184 | * 11/2005 | A61L 26/00 |
| JP | 07157427 | 12/1993 | |
| WO | WO 93/19739 | 10/1993 | |
| WO | WO 96/10389 | 4/1996 | |
| WO | WO 98/39042 | 9/1998 | |
| WO | WO 99/55287 | 11/1999 | |
| WO | WO 00/30630 | 6/2000 | |
| WO | WO 00/71089 | 11/2000 | |
| WO | WO-01/22907 A1 | 4/2001 | |
| WO | WO 01/30287 | 5/2001 | |
| WO | WO 01/37890 | 5/2001 | |
| WO | WO 01/50994 | 7/2001 | |
| WO | WO 01/54679 | 8/2001 | |
| WO | WO 2004/058329 | 7/2004 | |
| WO | WO 2005/032521 | 4/2005 | |

OTHER PUBLICATIONS

Levot et al., Evaluation of dressings to aid healing of mulesing wounds on sheep, Aust Vet J. Nov. 1989; 66(11) 358-361.

Pearse et al., Comparison of a liquid and a powder insecticidal dresssing to aid healing and prevent flystrike of mulesing would in lambs, Aust Vet J. May 1991; 68(5): 163-164.

Lubrizol, Neutralizing carbopol and pemulen polymers in aqueous and hydroalcoholic systems, Technical Data Sheet, TDS-237, Jan. 2002:1-3.

Bren, Helping wounds heal, U.S. Food and Drug Administration, May-Jun. 2002: 1-8.

Tuckley, The pharmacology of local anaesthetic agents, Pharmocology, Issue 4 (1994), Article 7.

Chapman, Progress towards a non-surgical alternative to the mules operation for the control of blowfly strike, ISSN 0043-7875/93. Wool Tech. Sheep Breed., 1993, 41:1-10.

Farquharson et al., Historic and current non-surgical alternatives to . . . , Proceedings of the Australian Sheep Veterinarians 2005—Gold Coast Conference, vol. 15, pp. 157-161.

Ilkiw, Local anesthesia and local anesthetic techniques, World Small Animal Veterinary Association Worl Congress—Vancouver 2001:1-5.

Glattes, Rudolph C et al, "A simple, accurate method to conform placement of intra-articular knew injection," American Journal of Sports Medicine, American Ortopaedic Society for Sports Medicine, vol. 32, No. 4, Jun. 1, 2004, pp. 1029-1031.

* cited by examiner

TOPICAL ANESTHETIC COMPOSITION

CROSS-REFERENCE TO PRIOR APPLICATIONS

This application is a continuation-in-part of international application PCT/AU2006/000336 filed Mar. 15, 2006 which designated the U.S. and additionally claims priority from Australian provisional patent application 2005901250 filed Mar. 15, 2005, Australian provisional patent application 2005902296 filed May 6, 2005, Australian provisional patent application 2005905062 filed Sep. 14, 2005, and Australian provisional patent application 2005906965 filed Dec. 12, 2005, the content of which applications are incorporated herein by reference.

U.S. GOVERNMENT SUPPORT

Not Applicable

BACKGROUND OF THE INVENTION

1. Technical Area

This invention relates to a composition comprising a local anesthetic agent in combination with a detectable marker. In particular, the invention concerns a composition for topical application to a subject and the presence of the anesthetic agent on the subject is indicated by the detectable marker.

2. Description of the Background

Local anesthetics used in animal husbandry procedures are usually in the form of injectable compositions. Injectable compositions have disadvantages in that they cause pain to the animal during administration and pose risks to the animal due to inadvertent injury or toxicity if incorrectly applied. They can be difficult or dangerous to administer. They can increase animal stress by prolonging handling times. They can increase the risk of injury to the handler due to needle stick or prolonged handling times. In addition, they are single use and are not convenient for administration to a large number of animals at the one time. They may require administration by a veterinarian, and it may be difficult to determine whether administration has been carried out correctly. It is for these reasons that most husbandry procedures (e.g. mulesing, shearing, castration, tail docking, ear tagging, de-horning, branding and marking) are performed without anesthesia It is an object of the present invention to provide a topical anesthetic composition, or a method of administering a topical anesthetic composition, which minimizes or ameliorates at least one of the disadvantages referred to above, or to provide the public with a useful or commercial choice.

SUMMARY OF THE INVENTION

According to a first aspect of the present invention, there is provided a topical anesthetic composition comprising at least one local anesthetic agent and a detectable marker, wherein when the composition is topically applied to a subject the presence of the anesthetic agent on the subject is indicated by the detectable marker.

According to a second aspect of the present invention, there is provided a method for anaesthetizing a subject, said method comprising the step of applying topically to the subject a composition comprising at least one local anesthetic agent and a detectable marker, wherein the presence of the anesthetic agent on the subject is indicated by the detectable marker.

According to a third aspect of the present invention, there is provided the use of a composition comprising at least one local anesthetic agent and a detectable marker in the preparation of a topical medicament for providing anesthesia to a subject, wherein the presence of the anesthetic agent on the subject is indicated by the detectable marker.

According to a fourth aspect of the present invention, there is provide a method for preparing a topical anesthetic composition for use on a subject, wherein said method comprises the step of combining at least one local anesthetic agent together with a detectable marker, whereby the presence of the anesthetic agent on the subject is indicated by the detectable marker.

Any suitable type of anesthetic agent or combination of agents can be used. Lignocaine, chloroprocaine, mepivacaine, bupivacaine, articaine, etidocaine, levobupivacaine, tetracaine, prilocalne, benzocaine, ropivacaine, cocaine, oxyprocaine, hexylcaine, dibucaine, piperocaine and procaine and pharmaceutically acceptable acids, bases and salts thereof, for instance, may be suitable anesthetic agents.

Other potential anesthetic agents include: butamben, butambenpicrate, dimethisoquin hydrochloride, diperodon, diphenhydramine, dyclonine, ketamine, methapyriline, p-buthylaminobenzoic acid, 2-(die-ethylamino) ethyl ester hydrochloride, pramoxine and tripelennamine.

The anesthetic composition preferably provides maximum anesthesia with minimal risk of toxicity. The formulation of the composition can be varied, as required, for potency, speed of onset and duration of anesthetic action.

Preferably, the composition comprises at least one local anesthetic agent having a rapid onset of action and at least one local anesthetic agent having a long duration of action.

Anesthetic agents that usually have a rapid onset of action (usually between about 5-10 minutes) include lignocaine, prilocalne, amethocaine and cocaine.

Anesthetic agents that usually have a much slower onset of action but a much greater duration of action (usually between about 4-12 hours of anesthesia) include bupivacaine amethocaine/tetracaine. Bupivacaine may typically provide up to about 6-12 hours of anesthesia, depending on the method of administration.

Any suitable amount of lignocaine can be used in the composition but preferably about 1-10 weight/volume % lignocaine is used. Preferably, about 2-8 weight/volume % lignocaine is used as the anesthetic agent in those situations where a rapid onset of action is required. More preferably, about 5% lignocaine is used.

The composition can further comprise any suitable amount of bupivacaine if lignocaine has an inadequate duration of action. Preferably, the composition comprises about 0.1-5 weight/volume % bupivacaine, and more preferably about 0.5% bupivacaine.

Preferably, the composition is used for anaesthetizing an open wound, preferably an open skin wound, such as a laceration, surgical incision, abrasion, ulcer or burn of the subject. Such a wound is likely to actively bleed or weep. The term "open skin wound" is to be understood as excluding a mucous membrane wound of the alimentary and respiratory tracts and eyes, but including a skin laceration, surgical incision, ulcer, abrasion or burn and exposed underlying tissues. However, the composition may be applied to a sutured skin wound and the like—whenever anesthesia of a skin wound is required.

The composition can further include a vasoconstrictor to decrease the rate of vascular absorption of the anesthetic agent, so to improve the depth and duration of anesthesia, to reduce bleeding from an open wound of the subject, as well as to reduce systemic toxicity. Any suitable type of vasoconstrictor can be used. Suitable vasoconstrictors include, for instance, adrenaline (epinephrine), noradrenalin (norepinephrine) and fenylpressin. Preferably, the composition includes about 1:1000-1:80,000 adrenalin, and more preferably 1:2,000 adrenalin.

The composition can include one or more other active ingredients. An active ingredient, as defined herein, is a compound that provides benefit to the subject. The active ingredient can be, for instance, an antibody, analgesic, anticoagulant, antiproliferative, anti-inflammatory, cytokine, cytotoxin, growth factor, interferon, haemostatic agent, hormone, lipid, demineralized bone or bone morphogenetic protein, cartilage inducing factor, oligonucleotide, polymer, polysaccharide, polypeptide, protease inhibitor, vitamin, mineral, antiseptic agent, insecticide or insect repellent, antibiotic or antifungal agent.

Potential analgesic anti-inflammatory agents include the following: acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexemacpiroxicam, phenylbutazone, oxyphenbutazone, clofezone, pentazocine, mepirizole, hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, and tolmetin.

The composition preferably includes an antiseptic agent to, amongst other things, minimize wound contamination and infection. Any suitable type of antiseptic agent can be used. Suitable antiseptic agents include cetrimide, povidone-iodine, chlorhexidine, iodine, benzalkonium chloride, benzoic acid, nitrofurazone, benzoyl peroxide, hydrogen peroxide, hexachlorophene, phenol, resorcinol and cetylpyridinium chloride. It is possible that a strongly colored antiseptic such as iodine can also be the detectable marker.

The composition preferably includes an insecticide or insect repellent to stop insects from infesting a wound of the subject. Any suitable type of insecticide or insect repellent can be used. Examples of suitable insecticides include: trichlorfon, triflumeron, fenthion, bendiocarb, cyromazine, dislubenzuron, dicyclanil, fluazuron, amitraz, deltamethrin, cypermethrin, chlorfenbinphos, flumethrin, ivermectin, abermectin, avermectin, doramectin, moxidectin, zeti-cypermethrin, diazinon, spinosad, imidacloprid, nitenpyran, pyriproxysen, sipronil, cythioate, lufenuron, selamectin, milbemycin oxime, chlorpyrifos, coumaphos, propetamphos, alpha-cypermethrin, high cis cypermethrin, ivermectin, diflubenzuron, cyclodiene, carbamate and benzoyl urea.

Any suitable type of detectable marker can be used. The marker may be, for instance, visible to the eye or visible under UV light. The detectable marker is preferably a visual marker and can be visible either before the composition is applied to the subject and/or after the composition is applied to the subject. The detectable marker is preferably a colorant. The colorant can be a pigment and/or dye. Suitable colorants include, for example, common food dyes or the ORCODERM®, ORCOBRITE® and ORCOFUR® lines of pigments and dyes sold by the Organic Dyestuffs Corporation.

Preferably, the detectable marker is non-toxic and will not permanently stain the skin or animal hide or surrounding hair, fur or wool.

The subject can be a human. The subject can be an animal such as a sheep, horse, cow, goat, pig, dog or cat. The subject can be another type of animal.

The composition can be used for an animal husbandry procedure. The procedure can be, for example, mulesing, shearing, castration, tail docking, ear tagging, de-horning, branding, marking, or treating an open wound, e.g. caused by shearing. Preferably, the composition is used for mulesing which is performed so as to prevent flystrike.

The composition can be applied to the subject in any suitable form. The composition can be, for example, in form of an ointment, gel, lotion, creme, cream, stick, emulsion, powder, paste, solution, suspension, spray-solution, spray-on gel, creme, foam or aerosol. The composition can be in a sustained-release form, whereby actives are slowly released over an extended period of time. The composition can be incorporated into a bandage or plaster.

Preferably, the composition is applied to the subject as a spray-on gel, emulsion, powder, solution, creme, suspension or foam, so as to disturb a wound of the subject as little as possible. Preferably, the composition is applied as a metered dose.

The composition can be applied to the subject as a spray-on gel so as to minimize pain related to touching or handling a wound (caused by mulesing, for example), minimize the risk of infection from skin contamination and so that the wound need not be disturbed more than necessary. Alternatively, the composition can be applied as a gel by hand, or squeezed from a tube to fill a wound caused, say, during a de-horning procedure.

According to a fifth aspect of the present invention, there is provided a method for anaesthetizing a large numbers of animals for a husbandry procedure in a short period of time, said method comprising the steps of:
creating an open skin wound on each said animal in accordance with the husbandry procedure; and
spraying onto the skin wound of each said animal a composition comprising:
a local anesthetic agent;
at least one ingredient for making the composition viscous and adhere to the skin wound;
a vasoconstrictor; and
a detectable marker,
wherein when the composition is sprayed onto the skin wound, the presence of the local anesthetic agent is indicated by the detectable marker.

The animal husbandry procedure is preferably selected from the group consisting of mulesing, shearing, castration, tail docking, ear tagging, de-horning, branding and marking.

Such a method allows for the high throughput of animals due to the unique properties of the composition; namely, it can be sprayed on rather than needle-injected, it is wound-adherent and its application to the wound can be easily detected.

Depending on the form of the composition, the composition can include one or more of the following types of ingredients: aqueous or oily diluent, carrier, excipient or base; buffer; bittering agent (i.e. foul-tasting agent); suspending agent; emulsifier; emollient; humectant; stabilizing agent; dispersing agent; solubilizer; skin conditioning agent; skin protectant; skin penetration enhancer; fragrance; preservative; propellant; sunscreen agent; surfactant; textural modifier; and waterproofing agent.

Suitable oily or aqueous bases, carriers, diluents and excipients are inert and physiologically acceptable and include, for example: bacteriostatic saline (saline containing benzyl alcohol), cetomacrogol, cetyl alcohol, glycerine, lanolin, petrolatum based creams, gels, hydrogels, saline, short chain alcohols and glycols (e.g. ethyl alcohol and propylene glycol), and water.

Either water in oil or oil in water emulsions can be used. Examples of suitable surfactants and emulsifying agents include: non-ionic ethoxylated and non-ethoxylated surfactants, abietic acid, almond oil PEG, beeswax, butylglucoside caprate, C18-C36 acid glycol ester, C9-C15 alkyl phosphate, caprylic/capric triglyceride PEG-4 esters, cetomacrogol, ceteareth-7, ceterearth-20, cetyl phosphate, cetyl stearyl alcohol, corn oil PEG esters, DEA-cetyl phosphate, dextrin laurate, dilaureth-7 citrate, dimyristyl phosphate, glycereth-17 cocoate, glyceryl erucate, glycerol, glyceryl laurate, G.M.S. acid stable, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPGs, raffinose myristate, sodium caproyl lactylate, sodium caprylate, sodium cocoate, sodium isostearate, sodium tocopheryl phosphate, steareths, TEA-C12-C13 pareth-3 sulfate, tri-C12-C15 pareth-6 phosphate, and trideceths.

The composition can include one or more types of preservative. A suitable preservative, for example, can be: benzalkonium chloride, benzoic acid, benzothonium chloride, benzyl alcohol, 2-bromo-2-nitropropane-1,3-diol, bronopol, butylated hydroxyanisole, butylated hydroxytoluene, butyl paraben, chlorophene, chlorphenesin, diazolidinyl urea, DMDM hydantoin, ethyl paraben, formaldehyde-releasing preservative, hydroquinone, iodopropynyl butylcarbamate, imidazolidinyl urea, methyldibromo glutaronitrile, methylhydroquinone, methylisothiazolinone, methyl paraben, nitrosamines, o-cymen-5-ol, phenoxyethanol, propyl paraben, quaternium-15, sodium benzoate, sodium dehydroacetate, sodium hydroxymethylglycinate, sodium metabisulfite, and sodium sulfite. Preferably, the composition includes the reducing agent sodium metabisulfite so as to enhance the stability of the vasoconstrictor.

A skin conditioning agent, as defined herein, improves dry or damaged skin. Such agents, for example, include: acetyl cysteine, N-acetyl dihydrosphingosine, acrylates/behenyl acrylate/dimethicone acrylate copolymer, adenosine, adenosine cyclic phosphate, adensosine phosphate, adenosine triphosphate, alanine, albumen, algae extract, allantoin and derivatives, aloe barbadensis extracts, aluminum PCA, amyloglucosidase, arbutin, arginine, azulene, bromelain, buttermilk powder, butylene glycol, caffeine, calcium gluconate, capsaicin, carbocysteine, carnosine, beta-carotene, casein, catalase, cephalins, ceramides, chamomilla recutita (matricaria) flower extract, cholecalciferol, cholesteryl esters, cocobetaine, coenzyme A, corn starch modified, crystallins, cycloethoxymethicone, cysteine DNA, cytochrome C, darutoside, dextran sulfate, dimethicone copolyols, dimethylsilanol hyaluronate, DNA, elastin, elastin amino acids, epidermal growth factor, ergocalciferol, ergosterol, ethylhexyl PCA, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, kinetin, lactoferrin, lanosterol, lauryl PCA, lecithin, linoleic acid, linolenic acid, lipase, lysine, lysozyme, malt extract, maltodextrin, melanin, methionine, mineral salts, niacin, niacinamide, oat amino acids, oryzanol, palmitoyl hydrolyzed proteins, pancreatin, papain, PEG, pepsin, phospholipids, phytosterols, placental enzymes, placental lipids, pyridoxal 5-phosphate, quercetin, resorcinol acetate, riboflavin, RNA, *saccharomyces* lysate extract, silk amino acids, sorbitol, sphingolipids, stearamidopropyl betaine, stearyl palmitate, tocopherol, tocopheryl acetate, tocopheryl linoleate, ubiquinone, *vitis vinifera* (grape) seed oil, wheat amino acids, xanthan gum, and zinc gluconate.

The composition can include a skin penetration enhancer for enhancing the penetration of active ingredients, such as the anesthetic agent. Any suitable type of enhancer can be used. Examples of suitable enhancers may include solvents, detergents or low carbon alcohols such as dimethylsulfoxide, oleyl alcohol, propylene glycol, methyl pyrrolidone and dodecylazyl cycloheptan 2-one.

Examples of thickening or viscosity increasing agents include: acrylamides copolymer, agarose, amylopectin, bentonite, calcium alginate, calcium carboxymethyl cellulose, carbomer, carboxymethyl chitin, castor oil derivatives, cellulose gum, cellulosic preparation, cetyl alcohol, cetostearyl alcohol, coconut oil, dextrin, gelatin, hydrogenated tallow, hydroxy cellulose, hydroxyethylcellulose, hydroxypropylcellulose, hydroxpropyl starch, inorganic thixotrope, magnesium alginate, methylcellulose, microcrystalline cellulose, modified clays, paraffin, pectin, various PEG's, polyacrylic acid, polymethacrylic acid, polyvinyl alcohol, quaternium ammonium compound of bentonite or zinc stearate, shea butter, sorbitol, various PPG's, sodium acrylates copolymer, sodium carrageenan, silicon dioxide, xanthum gum, and yeast beta-glucan.

Powders can incorporate a conventional powder base, such as kaolin, lactose, starch or talc.

The propellant can be, for example, a fluorochlorohydrocarbon such as dichlorodifluoromethane, difluoroethane or trichlorofluoromethane.

Preferably, the composition is in the form of a sticky, viscous gel. Preferably, the composition is in the form of a spray-on gel that can coat a wound of the subject and can maximize delivery of the active ingredients to the wound by way of staying moist and viscous (i.e. "sticky").

The composition can comprise a hydrophilic or hydroalcoholic gelling agent. Preferably, the composition comprises about 1 to 20 g per liter of at least one type of gum or cellulosic preparation. More preferably, the composition comprises a polyhydric alcohol in combination with a cellulosic preparation. Even more preferably, the composition comprises about 5 mg/mL hydroxy cellulose in combination with about 100 mg/mL non-crystallizing liquid sorbitol (70%).

In particular, the composition may comprise one or more of the following adhesives, thickening agents, gelling agents and/or viscosity increasing agents: acrylamides copolymer, agarose, amylopectin, calcium alginate, calcium carboxymethyl cellulose, carbomer, carboxymethyl chitin, castor oil derivatives, cellulose gum, cellulosic preparation, cetyl alcohol, cetostearyl alcohol, dextrin, gelatin, hydroxy cellulose, hydroxyethylcellulose, hydroxypropylcellulose, hydroxpropyl starch, inert sugar, magnesium alginate, methylcellulose, microcrystalline cellulose, pectin, PEG's, polyacrylic acid, polymethacrylic acid, polyvinyl alcohol, quaternium ammonium compound of bentonite or zinc stearate, sorbitol, PPG's, sodium acrylates copolymer, sodium carrageenan, xanthum gum, and yeast beta-glucan.

In a first preferred embodiment, the composition comprises:
about 100 mg/mL non-crystallizing liquid sorbitol (70%);
about 50.0 mg/mL lignocaine HCl;
about 5.0 mg/mL bupivacaine HCl;

about 1.5 mg/mL sodium metabisulfite;
0 mg/mL to about 5.0 mg/mL cetrimide;
about 45.0 μg/mL adrenaline tartrate;
about 5.0 mg/mL hydroxy cellulose; and
dye.

In a second preferred embodiment, the composition comprises:
about 100 mg/mL non-crystallizing liquid sorbitol (70%);
about 40.0 mg/mL lignocaine HCl;
about 1.5 mg/mL sodium metabisulfite;
0 mg/mL to about 5.0 mg/mL cetrimide;
about 36.0 μg/mL adrenaline tartrate;
about 5.0 mg/mL hydroxy cellulose; and
dye.

When the composition is used on animals, such as for mulesing, the composition preferably includes an insecticide or insect repellent. If used for, say, castration or tail docking, the composition may include a penetration enhancer.

The active ingredient also can be, for instance, a defleecing agent or skin scarring agent that causes temporary or permanent defleecing/wool or hair follicle destruction/skin scarring at the site of application (hereafter referred to as a "wounding agent").

The composition containing the wounding agent can be used for any suitable type of procedure (including surgical procedures) in which wool, fur or hair removal is required. The procedure can be, for example, chemical mulesing or chemical branding of animals. Preferably, the composition is used for chemical mulesing.

According to a sixth preferred aspect of the present invention, there is provided a topical anesthetic composition sprayable onto a skin wound such as a laceration, a surgical incision, an ulcer, an abrasion or a burn, said composition comprising:
a local anesthetic agent having a rapid onset of action;
at least one ingredient for making the composition viscous and adhere to the skin wound;
a vasoconstrictor; and
a detectable marker,
wherein when the composition is sprayed onto the skin wound, the presence of the local anesthetic agent is indicated by the detectable marker.

According to a seventh preferred aspect of the present invention, there is provided a method for anaesthetizing a skin wound of a subject, wherein said skin wound is selected from the group consisting of a laceration, a surgical incision, an ulcer, an abrasion and a burn, said method comprising the step of applying topically to the skin wound of the subject a composition comprising at least one local anesthetic agent and a detectable marker, wherein the presence of the anesthetic agent on the wound is indicated by the detectable marker.

According to an eighth preferred aspect of the present invention, there is provided a method for anaesthetizing a skin wound of a subject, wherein said skin wound is selected from the group consisting of a laceration, a surgical incision, an ulcer, an abrasion and a burn, said method comprising the step of spraying onto the skin wound of the subject a composition comprising:
a local anesthetic agent having a rapid onset of action;
at least one ingredient for making the composition viscous and adhere to the skin wound;
a vasoconstrictor; and
a detectable marker,
wherein when the composition is sprayed onto the skin wound, the presence of the local anesthetic agent is indicated by the detectable marker.

According to a ninth preferred aspect of the present invention, there is provided a method for providing anesthesia to a subject having a skin wound such as a laceration, a surgical incision, an ulcer, an abrasion or a burn, said method comprising the step of spraying onto the skin wound a composition comprising:
at least one local anesthetic agent;
a hydrophilic or hydroalcoholic gelling agent for making the composition viscous and adhere to the skin wound;
optionally an antiseptic agent;
a vasoconstrictor; and
a detectable marker,
wherein when the composition is sprayed onto the wound of the subject the presence of the anesthetic agent on the wound is indicated by the detectable marker.

According to a tenth preferred aspect of the present invention, there is provided a method for providing anesthesia to a subject having a wound caused by castration, mulesing, tail docking or dehorning, said method comprising the step of spraying onto the wound of the subject a composition comprising:
a local anesthetic agent having a rapid onset of action;
at least one ingredient for making the composition viscous and adhere to the wound;
a vasoconstrictor; and
a detectable marker,
wherein when the composition is sprayed onto the wound, the presence of the local anesthetic agent is indicated by the detectable marker.

According to an eleventh aspect of the present invention, there is provided a topical composition for both creating a wound on a subject and for alleviating pain due to the wound, said composition comprising: at least one wounding agent for creating a wound; at least one local anesthetic agent; and, a detectable marker, wherein the presence of the anesthetic agent on the subject is indicated by the detectable marker.

According to a twelfth aspect of the present invention, there is provided a method for both creating a wound on a subject and for alleviating pain due to the wound, said method comprising the step of applying topically to the subject a composition comprising: at least one wounding agent for creating a wound; at least one local anesthetic agent for anaesthetizing the wound; and a detectable marker, wherein the presence of the anesthetic agent on the subject is indicated by the detectable marker.

Any suitable type of wounding agent can be used. The wounding agent can comprise, for instance, one or more of the following: phenol; and, a cationic quaternary ammonium compound having the formula

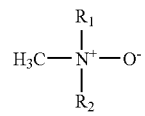

wherein R1 and R2 are alkyl having 8-10 carbon atoms.

Examples are didecylmethylamine oxide, didecyldimethylammonium chloride, dioctyldimethylammonium chloride, octyldecyldimethylammonium chloride, didecyldimethylammonium chloride, didecylmethylethylammonium chloride, didecylmethylpropylammonium chloride, didecylethylpropylammonium chloride, nonyltrimethylammonium bromide, tricapryl(trioctyl)methylammonium chloride, trioctylpropylammonium bromide, and Adogen 464-trimethyl C8-C10 quaternaryammonium chloride.

Further wounding agents are described in the specifications of Australian Patent No. 524658 to ICI Australia Limited and No. 647784 to Commonwealth Scientific and Industrial Research Organisation—the entire contents of which are hereby incorporated by reference.

Any suitable quantity of wounding agent or agents can be used. If the composition contains phenol, then it can comprise about 25-80% weight/volume of that compound. The phenol can be phenol, resorcinol or cresol, or a mixture of those compounds. The composition can include other ingredients as described in the specification of No. 524658.

If the composition contains a cationic quaternary ammonium compound, then it can comprise about 15-25% weight/weight of that compound. The composition can include other ingredients as described in the specification of No. 647784.

The composition can comprise other ingredients as described in respect of the other aspects of the invention.

Having broadly described the invention in its various embodiments, non-limiting examples of embodiments will now be given.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a means for anaesthetizing open wounds.

This invention has been developed primarily for anaesthetizing open wounds of animals, particularly those caused by husbandry procedures, and will therefore be described in this context. It is to be appreciated, however, that the invention may have general use in anaesthetizing open wounds (including lacerations, surgical incisions, abrasions, ulcers and burns) of animals and humans alike.

EXAMPLE 1

Formulation of a Topical Anesthetic Gel

This example describes the preparation of a topical anesthetic composition in the form of a spray-on gel. The composition has the following formulation:

| | |
|---|---|
| Purified water Sorbitol Liquid 70% Non-Crystallizing | 100.0 mg/mL |
| Lignocaine HCl | 40.0 mg/mL (4%) |
| Sodium Metabisulfite | 1.5 mg/mL |
| Cetrimide | 0-5.0 mg/mL |
| Adrenaline Tartrate | 36.0 µg/mL (1:2000) |
| Hydroxy Cellulose | Quantity to suit (q.s.) |
| Food Dye (e.g. blue) | q.s. |
| Purified water | to 1 mL |

The composition is prepared by combining the above ingredients to achieve the required color and consistency as required. The composition is then placed within a suitable spray-on applicator. The composition is viscous and, when applied, is in the form of a "sticky" gel.

Sorbitol functions as a thickener and a humectant and keeps the gel "sticky" after application. Sodium metabisulfite prevents oxidation of the adrenalin. Cetrimide is an antiseptic as well as a surfactant and humectant. Hydroxy cellulose functions as a thickener.

The hydroxy cellulose and sorbitol are primarily responsible for the gelatinous nature of the composition. Although typically the composition will comprise about 5 mg/mL hydroxy cellulose in combination with about 100 mg/mL non-crystallizing liquid sorbitol (70%), the composition can comprise anywhere from about 1 to 20 g per liter of at least one type of gum or cellulosic preparation. Typically, the composition will comprise a polyhydric alcohol in combination with a cellulosic preparation.

If desired, the composition can further comprise an anti-inflammatory agent (e.g. isoflupredone acetate), and/or an insecticide/insect repellent such as diazinon, cyromazine or spinosad (at about 1 mg/mL), and/or a skin penetrating enhancer, and/or a bittering agent.

EXAMPLE 2

Formulation of a Topical Anesthetic Gel Having a Long Duration of Action

This example describes the preparation of another topical anesthetic composition in the form of a spray-on gel and potentially having a longer duration of action than the composition of Example 1. The composition has the following formulation:

| | |
|---|---|
| Purified water Sorbitol Liquid 70% Non-Crystallizing | 100.0 mg/mL |
| Lignocaine HCl | 50.0 mg/mL (5%) |
| Bupivacaine HCl | 5.0 mg/mL (0.5%) |
| Sodium Metabisulfite | 1.5 mg/mL |
| Cetrimide | 0-5.0 mg/mL |
| Adrenaline Tartrate | 45.0 µg/mL |
| Food Dye (e.g. brilliant blue) | q.s. |
| Hydroxy Cellulose | q.s. |
| Purified water | to 1 mL |

The composition is prepared by combining the above ingredients to achieve the required color and consistency as required. The composition is then placed within a suitable spray-on applicator. Again, the composition is in the form of a "sticky" gel.

If desired, the composition can further comprise an anti-inflammatory agent, and/or an insecticide/insect repellent, and/or a skin penetrating enhancer, and/or a bittering agent.

EXAMPLE 3

Formulation of a Topical Anesthetic Crème Having a Long Duration of Action

This example describes the preparation of another topical anesthetic composition in the form of a spray-on crème. The composition has the following formulation:

| | |
|---|---|
| Cetyl Alcohol | 78.00 mg/mL |
| Paraffin Wax | 135.00 mg/mL |
| Glycerol | 75.00 mg/mL |
| Lauryl Sulfate | 10.00 mg/Ml |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0-5.0 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" crème.

If desired, the composition can further comprise an anti-inflammatory agent, and/or an insecticide/insect repellent, and/or a skin penetrating enhancer, and/or a bittering agent.

EXAMPLE 4

Formulation of a Topical Anesthetic Gel Having a Long Duration of Action

This example describes the preparation of another topical anesthetic composition in the form of a spray-on gel having a gum base. The composition has the following formulation:

| | |
|---|---|
| Xanthum Gum | 10.00 mg/mL |
| Gum Arabic | 1.00 mg/mL |
| Sorbitol Liquid | 100.00 mg/mL |
| Dye | q.s |
| Lignocaine HCl | 50.00 mg/mL |
| Bupivacaine HCl | 5.00 mg/mL |
| Sodium Metabisulfite | 1.50 mg/mL |
| Cetrimide | 0-5.0 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent, and/or an insecticide/insect repellent, and/or a skin penetrating enhancer, and/or a bittering agent.

EXAMPLE 5

Formulation of a Topical Anesthetic Gel Having a Long Duration of Action

This example describes the preparation of another topical anesthetic composition in the form of a spray-on gel having a polyacrylic acid base. The composition has the following formulation:

| | |
|---|---|
| Polyacrylic Acid | 10.00 mg/mL |
| Sodium Hydroxide | q.s. |
| Polyhydrogenated Castor Oil | 10.00 mg/mL |
| Sorbitol Liquid | 100.00 mg/mL |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0-5.0 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent, and/or an insecticide/insect repellent, and/or a skin penetrating enhancer, and/or a bittering agent.

EXAMPLE 6

Formulation of a Topical Anesthetic Gel Having an Insecticide and a Skin Penetrating Enhancer This example describes the preparation of another topical anesthetic composition in the form of a spray-on gel having an insecticide (spinosad) as well as a skin penetrating enhancer (propylene glycol). The composition has the following formulation:

| | |
|---|---|
| Cellulose | 5.00 mg/mL |
| Spinosad | 1.25 mg/mL |
| Propylene Glycol | 100.00 mg/mL |
| Sorbitol Liquid | 50.00 mg/mL |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0-5.0 mg/mL |
| Hydrochloric Acid 25% | q.s. |
| Adrenaline Acid Tartrate | 0.045 mg/mL |
| Purified Water | to 1 ml |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent and/or a bittering agent.

EXAMPLE 7

Use of a Topical Anesthetic Composition in Mulesing

This example describes the use of the composition of Example 1 or Example 2 in mulesing. It is to be appreciated that the compositions as described in the other examples could equally be used in a mulesing procedure.

If necessary, the breech area of the sheep is crutched of wool. Mulesing is then performed. This involves removing strips of skin from either side of the perineum and from the dorsal surface of the tail. The tail may be docked at the same time. The composition is then immediately applied to the surgical wound as a colored gel by a metered dose spray-on pump pack or trigger spray bottle. About 5-15 mLs of the composition is applied, depending on the size of the wound and the animal.

The lignocaine/bupivacaine/adrenaline combination in a sustained release gel base provides rapid as well as prolonged pain relief for a period of at least 8 hours. The dye indicates the area of the sheep that has been anaesthetized. The antiseptic cetrimide helps minimize contamination of the wound with bacteria. The insecticide, if present, can repel insects such as blowflies and prevent flystrike. The gel remains as a "sticky" coat on the wound protecting it and maximizing extended delivery of the active ingredients to the wound. Moreover, preliminary experiments on lambs undergoing mulesing indicate that the fact that the gel coats the wound (i.e. nerve endings), numbing of pain occurs after about 4 hours independently of the anesthetic agent/s; this therefore contributes to and enhances the anesthetic effect of the formulation.

If the composition contains an insecticide (e.g. the composition as described in Example 6), then it can be further applied onto the woolen skin surrounding the wound/cut skin edges for a distance of about 2-10 cm.

EXAMPLE 8

Use of a Topical Anesthetic Composition for Castration

This example describes the use of the composition of any one of Examples 1-6, but preferably Example 6, for animal castration.

The animal should be held firmly and securely in a cradle or restraint designed for routine surgical castration. An incision is made in the scrotal sac and the testes and chordal tissue exposed as per routine surgical castration. The composition is then sprayed onto the chordal tissue so as to fully coat it, particularly at the site of intended incision and along the length of chordal tissue that will remain and retract into the scrotal sac after the testes are excised. Depending on the size of the animal, approximately 0.5-2 mLs of spray-on composition is used. The testes are then excised by cutting through the chordal tissue at the level where the composition has been applied, using routine surgical castration technique. The empty scrotal sac and edges of the skin incision are then sprayed with an additional dose of the composition so as to fill the sac and coat the cut skin edges. Depending on the size of the animal, approximately 1-4 mLs of spray-on composition is used.

EXAMPLE 9

Use of a Topical Anesthetic Composition for Shearing Cuts, Skin Lacerations and Superficial Burns This example describes the use of the composition of any one of Examples 1-6 for shearing cuts, skin lacerations and superficial burns.

Where a significant skin laceration or superficial (1st or second degree) burn occurs, such as during shearing or branding, the composition may be sprayed directly onto the wound so as to coat the wound and cover the cut skin edges. The spray is applied by metered dose. The volume applied will vary depending on the size of the wound and animal. For instance, a total dose of 50 mg/kg of lignocaine should not be exceeded for sheep.

EXAMPLE 10

Use of a Topical Anesthetic Composition for Dehorning

This example describes the use of the composition of any one of Examples 1-6 for dehorning.

Where dehorning of animals is carried out leaving a raw, bleeding bed of tissue, the composition may be applied directly to the raw tissue bed immediately following dehorning either by metered spray, or by metered squeeze application of the composition in a thick gel, creme or paste so as to cover the entire exposed tissue bed and remain in contact with it. Estimated volumes required are 1-3 mLs per dehorned tissue bed depending on the size of the wound. The total dose applied should not exceed safety limits of mg/kg lignocaine (topically applied) for the animal species involved.

EXAMPLE 11

Use of a Topical Anesthetic Composition for Treating Flystrike Wounds

This example describes the use of a topical anesthetic composition containing an insecticide, such as the composition described in Example 6, for treating wounds resulting from flystrike.

Flystrike wounds are very painful for sheep. Current practices involve cutting away all wool in the flystruck area and then spraying or applying an insecticide to kill the maggots and eggs. Pain is not addressed. A combination agent of a maggot killing insecticide plus an anesthetic agent, such as the composition described in Example 6, may be applied to kill maggots and relieve pain and aid in wound healing.

The method entails cutting wool away from an affected area and scraping maggots off as per routine flystrike management. The composition is sprayed by metered dose to cover the affected area. The volume applied will vary depending on the size of the wound and animal. For instance, a total dose of 50 mg/kg of lignocaine should not be exceeded for sheep. In cases of large flystrike wounds where it is anticipated that an excessive volume of the composition is required to cover the wound (e.g. >1 ml/kg/sheep), a lower concentration composition should be used containing, for example, 1 or 2% lignocaine with insecticide.

EXAMPLE 12

Formulation of Topical Anesthetic Compositions for Chemical Mulesing or Branding This example describes various compositions for use in chemical mulesing or branding.

Each composition for use in chemical mulesing or branding includes a wounding agent, such as a cationic quaternary ammonium compound, in combination with one or more anesthetic agents as described in the above examples.

Various formulations are given below:

1. Dimethyl Ammonium Chlorides with Emollients

| | |
|---|---|
| Dimethyl Ammonium Chlorides | 250.00 mg/mL |
| Propylene Glycol | 150.00 mg/mL |
| Sorbitol Liquid | 100.00 mg/mL |
| Dye | q.s. |
| Glycerol | 400.00 mg/mL |
| Purified Water | to 1 mL |

This mixture is then admixed with, say, the composition of Example 1 or 2.

2. Dimethyl Ammonium Chlorides in a Crème Base:

| | |
|---|---|
| Dimethyl Ammonium Chlorides | 250.00 mg/mL |
| Cetyl Alcohol | 80.00 mg/mL |
| Propylene Glycol | 100.00 mg/mL |
| Dye | q.s. |
| Purified Water | to 1 mL |

This mixture is then admixed with, say, the composition of Example 1 or 2.

3. Dimethyl Ammonium Chlorides in Polyacrylic Acid Base:

| | |
|---|---|
| Dimethyl Ammonium Chlorides | 250.00 mg/mL |
| Polyacrylic Acid | 10.00 mg/mL |
| Sodium Hydroxide | q.s. |
| Propylene Glycol | 100.00 mg/mL |
| Dye | q.s. |
| Purified Water | to 1 mL |

This mixture is then admixed with, say, the composition of Example 1 or 2.

Each chemical mulesing/branding composition is prepared by combining the above ingredients to achieve the required color and consistency as required. The composition is then applied against the skin with a squeeze-on applicator which is combed through the wool or fur over the intended wound area. The composition is viscous and, when applied, is in the form of a "sticky" base. The ammonium compound, where applied, creates a wound, and shortly thereafter the wound is anaesthetized as described in Example 7.

If desired, the composition can further comprise an insecticide/insect repellent such as cyromazine or spinosad (at about 1 mg/mL) and/or a skin penetrating enhancer.

Advantages of the present invention as exemplified include that the composition can be used to reduce or minimize pain in a large variety of animal husbandry procedures in which anesthetic agents are not currently used by virtue of being too impractical, dangerous, complex or costly.

Some of the exemplified anesthetic compositions can also be used on human wounds for effective pain relief.

Advantages to the animal: Any reduction in pain is likely to be of significant advantage to the animal. There is minimal risk of toxicity to the animal using this approach. The composition can be conveniently and safely applied to animals without the added pain and risk of injury associated with invasive methods of anesthetic delivery, and without increasing animal stress due to prolonged handling times. Preliminary studies in lambs have demonstrated a significant reduction in pain related behavior and a marked improvement in feeding and prevention of weight loss in treated lambs undergoing surgical mulesing.

Advantages to the handler: The composition provides a simple, practical and convenient method for reducing pain that their animals may experience. This is of advantage to the handler for moral and ethical reasons and because reducing animal pain can result in improved growth, handling and health outcomes for animals. The composition has advantages over invasive methods of anesthetic delivery because it can be quickly and easily administered to a large numbers of animals, even in remote locations with minimal additional cost and/or animal handling times. Simplicity of application, low risk of toxicity and ready visualization of the adequate wound covering is advantageous to the handler as successful application of the anesthetic can be readily achieved and monitored without risk of needle stick injury, without compromising animal breathing, mobility and/or recovery, and without the need for a veterinarian to administer the composition.

Other advantages of the present invention may be found in the applicants' co-pending PCT application entitled "A Topical Analgesic Composition", the entire contents of which are hereby incorporated by way of reference.

Throughout this specification, unless in the context of usage an alternative interpretation is required, the term "comprise" (and variants thereof such as "comprising" and "comprised") denotes the inclusion of a stated integer or integers but does not exclude the presence of another integer or other integers.

Any reference to publications cited in this specification is not an admission that the disclosures constitute common general knowledge in Australia or in other countries.

It will be appreciated by one of skill in the art that many changes can be made to the composition and uses exemplified above without departing from the broad ambit and scope of the invention.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A method for anesthetizing an open skin wound of a non-human animal, said wound having been caused by an animal husbandry or surgical procedure, comprising the step of topically applying to the wound a composition comprising:
    a) at least one local anesthetic agent;
    b) at least one thickener or viscosity increasing agent for making the composition viscous, adhere to the wound, and remain moist; and
    c) a detectable marker,
    wherein when the composition is topically applied to the wound, the presence of the anesthetic agent on the wound is indicated by the detectable marker.

2. The method of claim 1, wherein said at least one local anesthetic agent has a rapid onset of action, and said composition further comprises a local anesthetic agent having a long duration of action.

3. The method of claim 1, wherein the composition is sprayable onto the wound.

4. The method of claim 1, wherein the composition comprises ingredients selected from the group consisting of a hydrophilic or hydroalcoholic gelling agent, about 1 to 20 g per liter of at least one gum or cellulose, a polyhydric alcohol in combination with a cellulose, and hydroxy cellulose in combination with non-crystallizing liquid sorbitol.

5. The method of claim 1, wherein the composition comprises one or more ingredients selected from the group consisting of an antiseptic agent, an insecticide, an insect repellent, an anti-inflammatory agent, a skin penetrating enhancer, and a vasoconstrictor.

6. The method of claim 1, wherein said composition is in the form of a sprayable viscous gel that adheres to the wound and comprises:
    non-crystallizing liquid sorbitol and hydroxy cellulose to make the composition viscous and adherent;
    lignocaine as the at least one local anesthetic agent;
    bupivacaine;
    sodium metabisulfite;
    adrenaline; and
    dye as the detectable marker.

7. The method of claim 1, wherein the husbandry procedure is selected from the group consisting of mulesing, shearing, castration, tail docking, ear tagging, de-horning, branding and marking.

8. A method for anesthetizing an open skin wound of a non-human animal, said wound having been caused by an animal husbandry or surgical procedure, said method comprising the step of topically applying to the wound a composition comprising:
- a) a local anesthetic agent having a rapid onset of action;
- b) at least one thickener or viscosity increasing agent for making the composition viscous, remain moist, and adhere to the wound;
- c) a vasoconstrictor; and
- d) a detectable marker;

wherein when the composition is topically applied to the wound, the presence of the anesthetic agent is indicated by the detectable marker.

9. The method of claim 8, wherein said at least one ingredient comprises a hydrophilic or hydroalcoholic gelling agent.

10. The method of claim 8, wherein said composition further comprises a local anesthetic agent having a long duration of action.

11. The method of claim 8, wherein the husbandry procedure is selected from the group consisting of mulesing, shearing, castration, tail docking, ear tagging, de-horning, branding and marking.

12. The method of claim 1, wherein said at least one local anesthetic agent is tetracaine.

13. The method of claim 1, wherein said composition comprises one or more ingredients selected from the group consisting of:
  about 100 mg/mL non-crystallizing 70% liquid sorbitol;
  about 40.0 mg/mL to 50.0 mg/mL lignocaine HCI;
  0 mg/mL to about 5.0 mg/mL bupivacaine HCI;
  about 1.5 mg/mL sodium metabisulfite;
  0 mg/mL to about 5.0 mg/mL cetrimide;
  about 36.0 µg/mL to 45.0 µg/mL adrenaline tartrate; and
  about 5.0 mg/mL hydroxy cellulose.

14. The method of claim 8, wherein said composition comprises one or more ingredients selected from the group consisting of an antiseptic agent, an insecticide, an insect repellent, a skin penetrating enhancer, an antioxidant, and an anti-inflammatory agent.

15. The method of claim 8, wherein said at least one local anesthetic agent is tetracaine.

16. The method of claim 8, wherein said composition comprises one or more ingredients selected from the group consisting of:
  about 100 mg/mL non-crystallizing liquid 70%sorbitol;
  about 40.0 mg/mL to 50.0 mg/mL lignocaine HCI;
  0 mg/mL to about 5.0 mg/mL bupivacaine HCI;
  about 1.5 mg/mL sodium metabisulfite;
  0 mg/mL to about 5.0 mg/mL cetrimide;
  about 36.0 µg/mL to 45.0 µg/mL adrenaline tartrate; and
  about 5.0 mg/mL hydroxy cellulose.

* * * * *